United States Patent [19]

Tsai

[11] Patent Number: 5,076,785
[45] Date of Patent: Dec. 31, 1991

[54] DISPOSABLE DENTAL IMPRESSION TRAY

[76] Inventor: Yu-Son Tsai, No. 7-3, Lane 93, Chung Shan N. Road, Sec. 2, Taipei, China

[21] Appl. No.: 661,873

[22] Filed: Feb. 27, 1991

[51] Int. Cl.⁵ ............................................... A61C 9/00
[52] U.S. Cl. ................................................... 433/46
[58] Field of Search ..................................... 433/46, 45

[56] References Cited

U.S. PATENT DOCUMENTS

| | | | |
|---|---|---|---|
| 1,461,209 | 7/1923 | Bridges | 433/46 |
| 2,428,773 | 10/1947 | Beresin et al. | 433/46 |
| 2,577,513 | 12/1951 | Cunningham | 433/46 |
| 2,924,011 | 2/1960 | McAdoo | 433/46 |
| 4,368,040 | 1/1983 | Weissman | 433/45 |

FOREIGN PATENT DOCUMENTS 149778  1/1937  Austria ............................... 433/45

Primary Examiner—John J. Wilson
Attorney, Agent, or Firm—Michael N. Meller

[57] ABSTRACT

A dental impression tray made of plastic is proposed to be used in a disposable manner. The dental impression tray includes a tray body for securely holding a mold material, and a handle which is separately prepared and adapted to be connected with the tray body when in use. The handle is separated from the frame body while in storage, so that they can be separately stacked with less bulkiness in storage. The tray body and the handle are provided with a locking means which can securely connect the tray body and the handle into one unit.

3 Claims, 5 Drawing Sheets

DISPOSABLE DENTAL IMPRESSION TRAY

BACKGROUND OF THE INVENTION

This invention relates to a dental impression tray, and more particularly to a disposable dental impression tray having a tray body provided with a handle which is separately made and fixedly attached to the tray body.

In order to make an artificial tooth or teeth, or a denture, dentists usually first require a denture model. In order to make a denture model, a tray is used to take an impression of the configuration of the teeth of which the model is required. Conventionally, such a denture model is formed by the impression left in a dental impression tray filled with a self-hardening, gum-like compound; filled impression tray is inserted into the mouth and around the teeth before the compound has hardened; after the compound has hardened, the impression tray and hardened compound are pulled away from the teeth; the impressions made by the teeth in the hardened compound form a mold. A model material, such as a plaster, is cast in the impressions left in the mold, to obtain a denture model. As soon as the denture model has been obtained, the mold is removed from the tray and discarded, and the impression tray is used again.

Conventionally, the impression tray is made of a metal such as stainless steel; it is therefore relatively expensive. It has a tray body provided with a handle integrally formed with the tray body, when a number of impression trays are stacked together, they become bulky, particularly so if the handle is bent into a prescribed shape. Furthermore, as the impression tray is repeatedly used, it must be cleaned and sterilized each time it is re-used. Such a cleaning and sterilizing process is troublesome.

Therefore, it is the main object of this invention to present an improved dental impression tray which is relatively cheap and disposable.

It is another object of this invention to present an improved dental impression tray which has a tray body provided with a handle which is separately made, so that multiple tray bodies and handles can be separately stacked in storage to avoid bulkiness; the handle is fixedly attached to the tray body when the impression tray is to be used.

SUMMARY OF THE INVENTION

The dental impression tray of this invention includes a tray body made of a plastic material and a handle which is separately made and fixedly attached to the tray body in use, the handle also being made of a plastic material. The tray body has a generally U-shaped outer wall, a generally U-shaped inner wall, and a bottom plate integrally formed with and between the outer wall and the inner wall. At the central part of the outer wall an elongated holding slot is formed along the edge of the bottom plate and a tab is formed at the outer edge of the bottom plate, a pair of locking holes and a latch are formed in the bottom plate. The handle includes a handle plate and a handle stem integrally formed with the handle plate; the handle plate is provided with a pair of locking studs to engage with the pair of locking holes of the bottom plate of the tray body and a latch to fit in the latching hole of the tray body, and the handle stem is provided with holding jaws to fit into the holding slot of the outer wall of the frame body, the holding jaw being so formed to provide a recess to allow the tab of the tray body to fit therein. The handle is connected to the frame body by inserting the holding jaws of the handle into the holding slot of the frame body, thus allowing the tab of the tray body to fit into the recess of the handle, engaging the locking studs of the handle with the locking holes of the frame body, and allowing the latch of the tray body to fit into the latching hole of the handle.

DETAILED DESCRIPTION OF THE PREFERRED EMBODIMENTS

Figure 1:
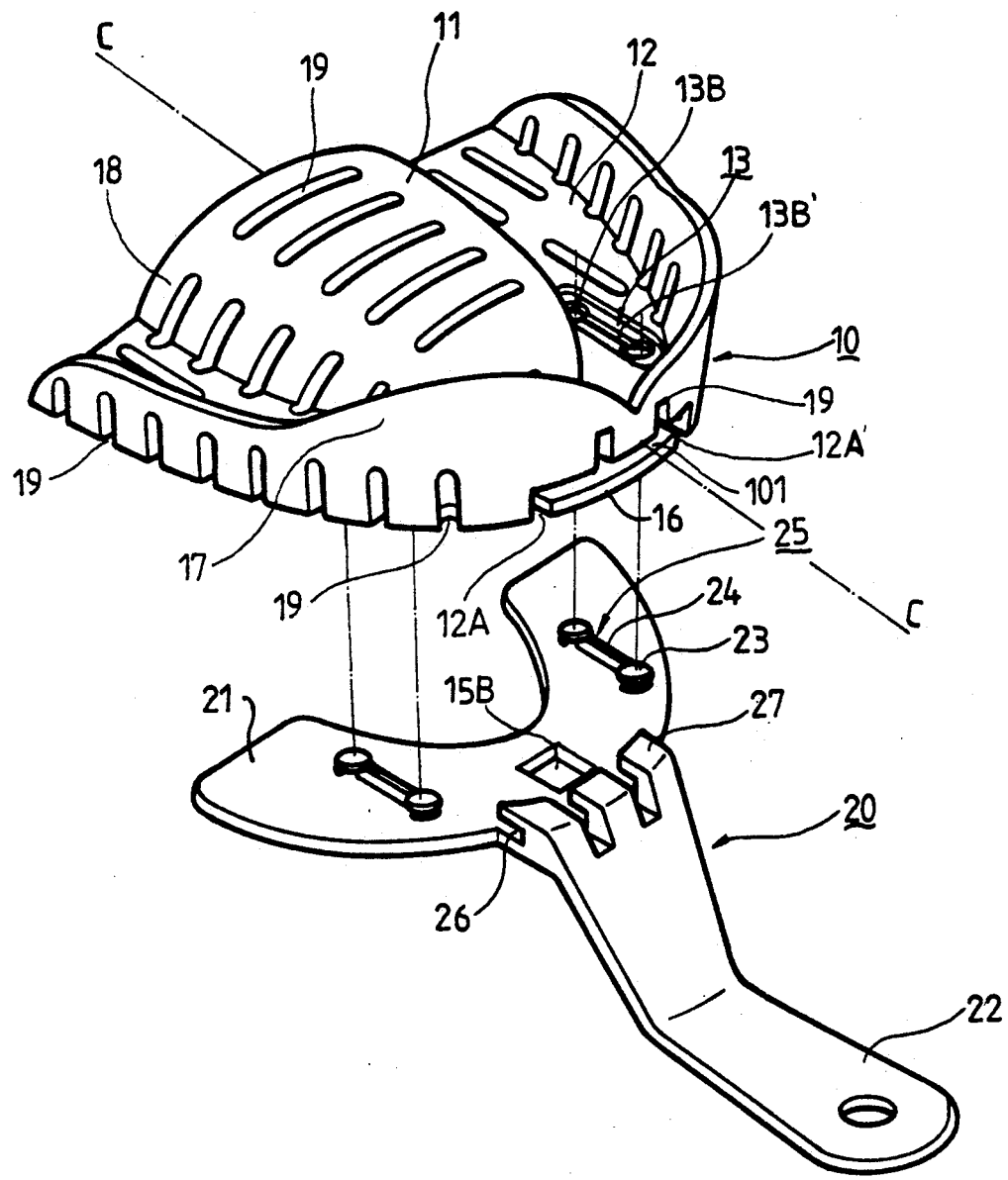
FIG. 1 is an exploded perspective view of the first embodiment of the dental impression tray of this invention.

Referring to FIG. 1, a first embodiment of the dental impression tray of this invention includes a tray body 10 made of a plastic material, and a handle 20 which is separately made and adapted to be firmly connected to tray body 10, the handle 20 also being made of a plastic material.

Tray body 10 has a generally U-shaped outer wall 17, a generally U-shaped inner wall 18 to correspond with outer wall 17, and a bottom plate 12 integrally formed with and between outer wall 17 and inner wall 18 so as to form a generally U-shaped trough adapted to receive therein a mold material such as a self-hardening gum. The first embodiment of the dental impression tray is intended for use in making a model of the upper teeth of a patient, so inner wall 18 of frame body 10 is provided with an integral central piece 11 to fit the upper roof of the mouth of the patient. A plurality of slots 19 are provided in various parts of the tray body to allow mold material to flow therein so as to firmly secure the mold material onto the tray body and prevent the mold material from separating from the tray body during the mold making process.

At a central part of outer wall 17, of tray body 10, an elongated holding slot 101 is formed along the edge of bottom plate 12, and two notches 12A and 12A' are provided in the bottom of plate 12 corresponding to the sides of holding slot 101, to define a tab 16. A pair of locking holes 13 are formed in bottom plate 12; in FIG. 1 only one locking hole 13 is shown, while another locking hole 13 is hidden behind outer wall 17.

Figure 2:
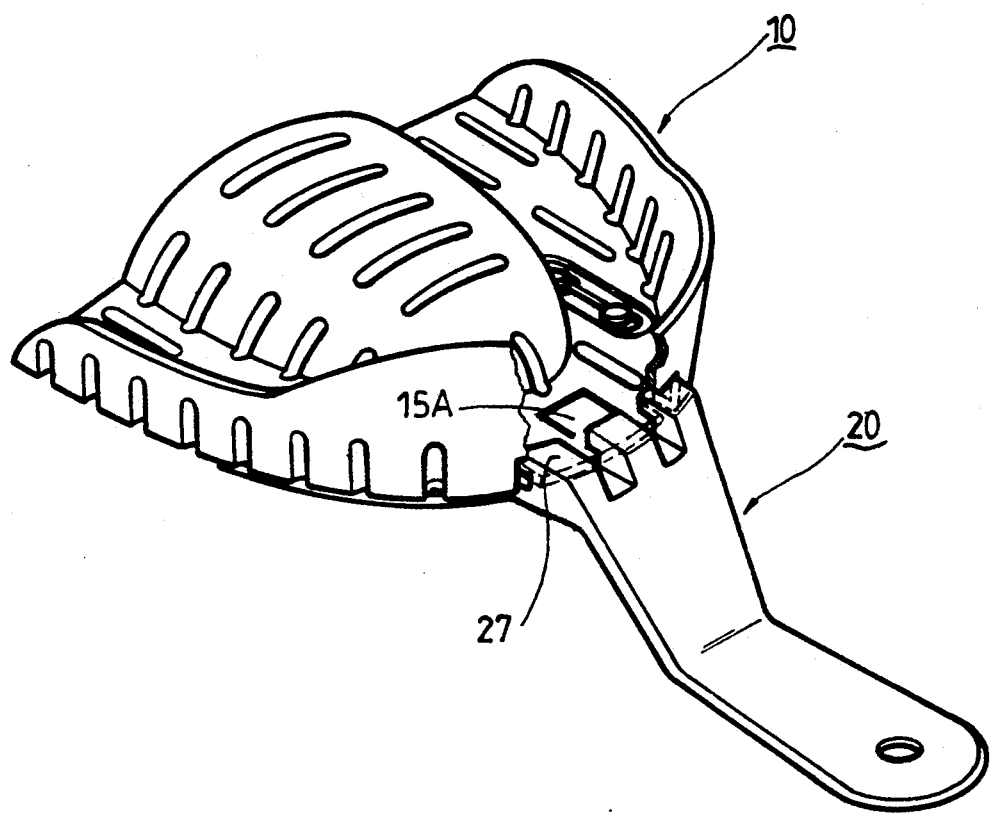
FIG. 2 is a perspective view of the dental impression tray of FIG. 1, in an assembled state, with the outer wall of the frame body partially cut away.
Figure 5:
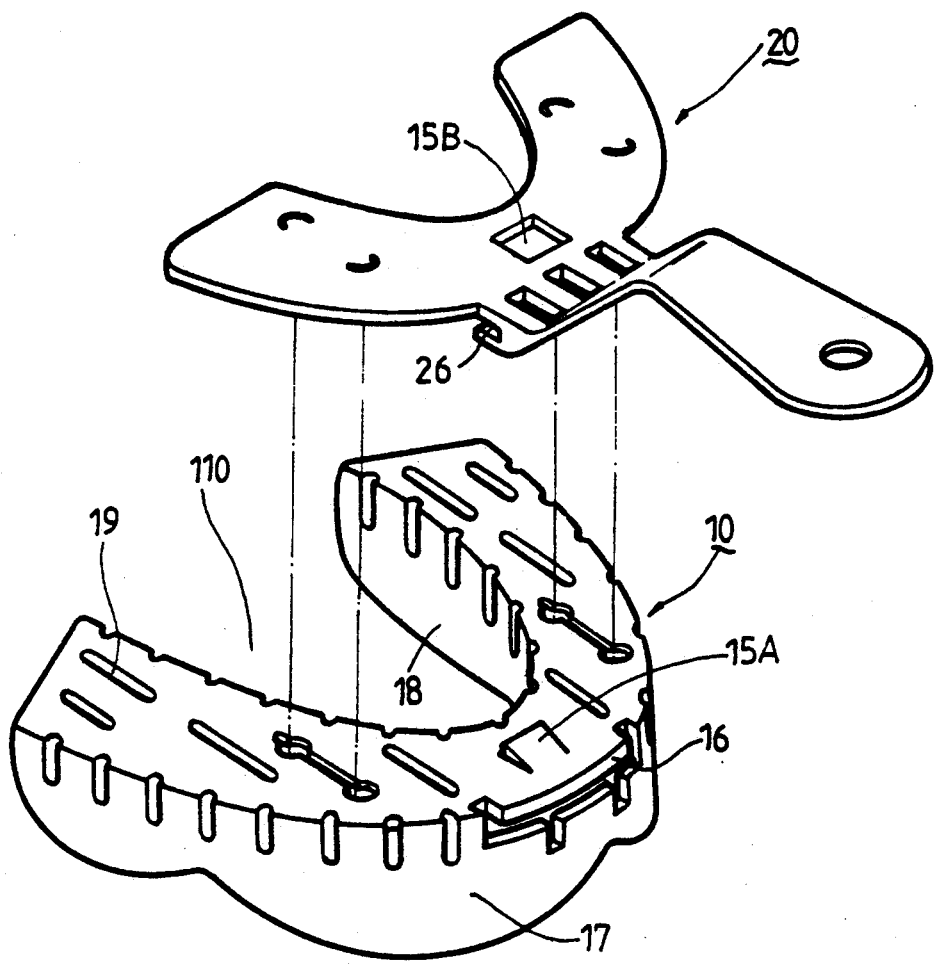
FIG. 5 is an exploded perspective view of a second embodiment of the dental impression tray of this invention, being viewed upside down.

As shown in FIG. 2, at a central part of the U-shaped bottom plate 12 of tray body 10, a latch 15A is provided by forming a generally U-shaped cut-through, latch 15A being extending towards the central part of tray body 12 and having a lower surface slightly inclined downwardly (as best shown in FIG. 5). Being so formed, latch 15A is resilient such that it is capable of snap-fitting into latching hole 15B of handle 20 which will be described later.

Figure 6:
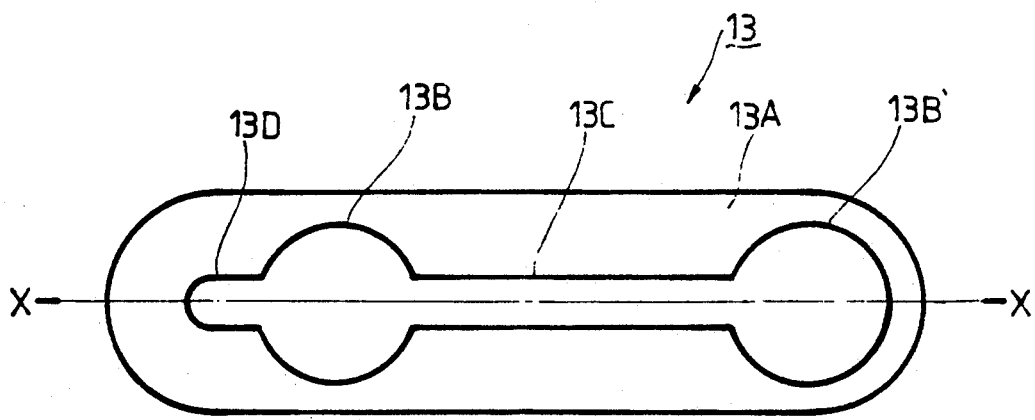
FIG. 6 is a schematic enlarged plan view of the locking hole.
Figure 7:
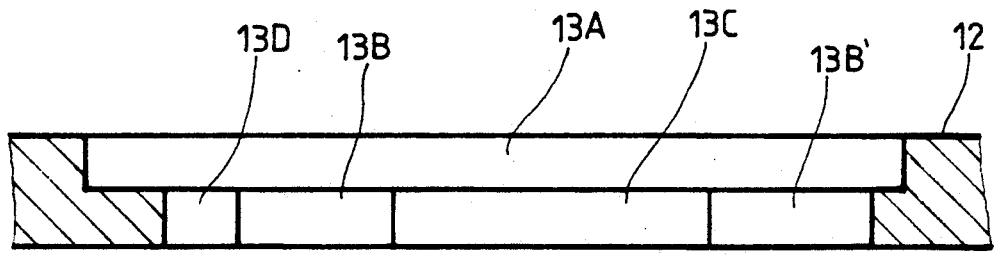
FIG. 7 is an enlarged cross-sectional view of the locking hole.

The details of locking hole 13 are shown in FIGS. 6 and 7. Locking hole 13 includes an elongated recess 13A formed on the upper side of bottom plate 12, two through holes 13B and 13B', an intermediate slot 13C formed between two through holes 13B and 13B', and an end slot 13D extending from the outer side of one through hole 13B. Locking hole 13 has a longitudinal center axis X—X parallel with longitudinal center axis C—C of frame body 10.

Handle 20 has a handle plate 21 and a handle stem 22 extending from handle plate 21. Handle stem 22 may be straight, or bent into a prescribed shape. On the upper part of handle stem 22 extending from handle plate 21, a plurality of holding jaws 27 are integrally formed with handle stem 22, holding jaws 27 extending in the direction opposite to handle stem 22 and providing a recess 26 between holding jaws 27 and the upper side of handle plate 21 in order to receive tab 16, when holding jaws 27 are fitted into holding slot 101 of frame body 10.

Figure 8:
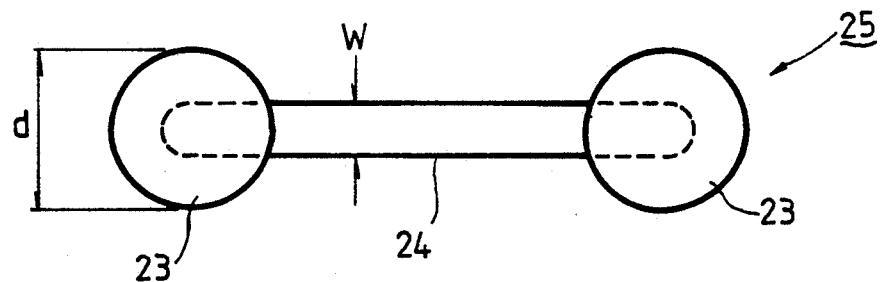
FIG. 8 is a schematic enlarged plan view of the locking stud.
Figure 9:
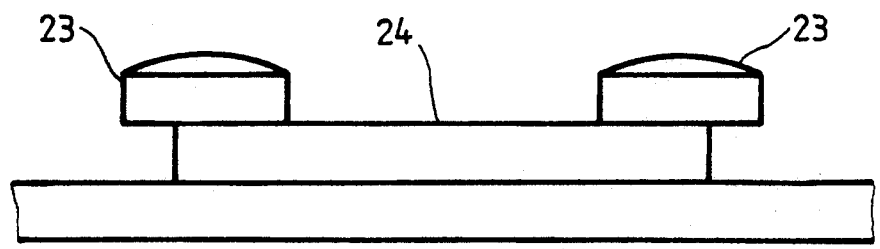
FIG. 9 is a schematic enlarged side view of the locking stud.

Handle plate 21 is provided with a pair of locking studs 25 and 25' to engage with locking holes 13 and 13' of frame body 10. Locking stud 25, as shown in FIGS. 1, 8, and 9, has an elongated rib 24 formed on the upper side of handle plate 21, and a circular head 23 on each one of the two ends of rib 24, circular head 23 having a diameter larger than the width of rib 24 and being adapted to fit in through hole 13B of locking hole 13, and rib 24 being adapted to slidably fit into intermediate slot 13C and end slot 13D of locking hole 13.

Handle plate 21 is further provided with a latching hole 15B, as shown in FIG. 1, to correspond with latch 15A of tray body 10 such that when handle 20 is connected with tray body 10 with holding jaws 27 completely inserted into holding slot 101 of tray body 10 and with locking studs 25 and 25' completely engaged with locking holes 13 and 13' of tray body 10, latch 15A of tray body 10 is allowed to snap-fit into latching hole 15B.

Figure 3:
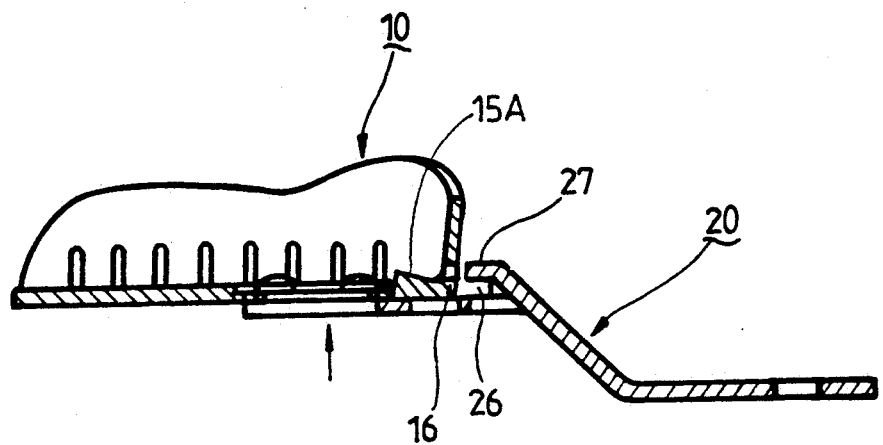
FIG. 3 is a longitudinal, cross-sectional view of the dental impression tray of FIG. 2, showing the initial stage of assembling the handle with the tray body.
Figure 4:
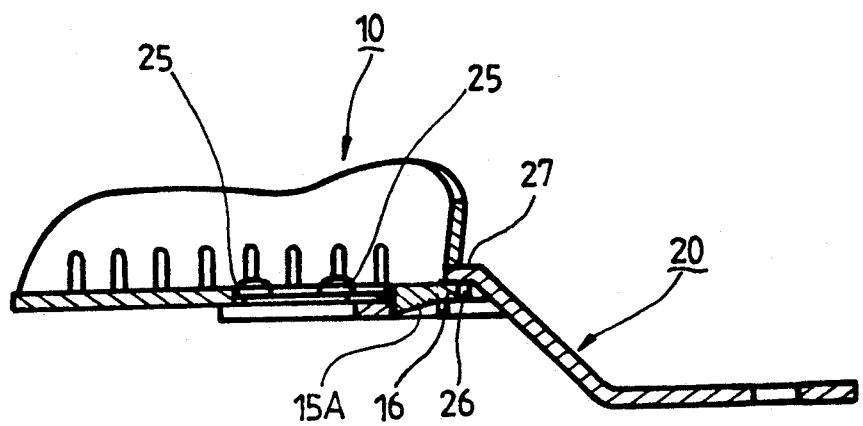
FIG. 4 is a longitudinal, cross-sectional view of the dental impression tray of FIG. 2, showing the final stage of assembling the handle with the tray body.

To connect (assemble) handle 20 and tray body 10, handle plate 21 of handle 20 is first attached from below to the bottom side of tray body 10, in such a manner that locking studs 25 of handle 20 fit in locking holes 13 of tray body 10, and holding jaws 27 of handle 20 are aligned with holding slot 101 of tray body 10, as shown in FIG. 3. At this stage, latch 15A of tray body 10 is pushed by an edge of latching hole 15B of handle 20 to become flush with bottom plate 12 of tray body 10. Next, handle 20 is pushed toward tray body 10, so as to cause rib 24 of locking stud 25 to slide along intermediate slot 13C of locking hole 13 to fit in end slot 13D, circular heads 13B and 13B' to slide along the bottom of recess 13A to engage with the upper edges of intermediate slot 13C and end slot 13D, holding jaws 27 to slide and fit into holding slot 101, and tab 16 to fit into recess 26, as shown in FIG. 4. In this position, latch 15A of tray body 10 in aligned with latching hole 15B of handle 20, so that latch 15A is allowed to spring back and snap-fit into latching hole 15B; as a result, handle 20 is firmly kept from being pulled in the reverse direction to separate from tray body 10. Holding jaws 27 and locking studs 25 firmly grip tray body 10 and prevent handle 20 from being separated from tray body 10 in a vertical direction. Therefore, handle 20 is firmly connected with tray body 10. The dental mold frame is now ready for use.

FIG. 5 shows a second embodiment of the dental impression tray of this invention. In this embodiment, central piece 11 of frame body 10 of the first embodiment is eliminated and a U-shaped cut-out 110 is formed in place of central piece 11. This embodiment enables the impression tray to be used in making a mold of the lower teeth as the U-shaped cut-out 110 provides a space adequate for receiving the root of the patient's tongue when the impression tray is inserted into the patient's mouth. It is also to be noted that the second embodiment can also be used for making a mold of the upper teeth.

A number of dental impression trays of this invention can be easily stored when they are not being used, with the tray bodies and handles separated from each other; they are less bulky in comparison with conventional dental mold frames, particularly when the handles are bent into a prescribed shape.

Though preferred embodiments have been described and illustrated in the drawings, modifications are possible; slots 19 can be replaced by ribs, hooks, or holes; locking stud 25 and locking hole 13 can be replaced by other known locking devices; holding jaws 27 can be made in a single piece; notches 12A and 12A' may be eliminated; the combination of holding jaws 27, holding slot 101, and tab 16 can be replaced by a snap-in-type hook. These modifications are all within the scope of the appended claims.

What is claimed is:

1. A dental impression tray made of a plastic material, comprising:
  a tray body having a generally U-shaped trough for holding a mold material and a bottom plate,
  a handle separately prepared and adapted to be connected to said frame body when in use, said handle having a handle plate and a handle stem integrally formed with said handle plate,
  said tray body and said handle being provided with locking means to prevent said handle from being separated from said tray body after said handle has been connected to said tray body,
  said locking means comprising:
  a pair of locking holes in said bottom plate of said tray body;
  a pair of locking studs on said handle plate of said handle;
  a holding slot in said tray body;
  a holding jaw on said handle stem of said handle;
  a latch on said bottom plate of said tray body;
  a latch hole in said handle plate of said handle;
  said locking studs being adapted to fit into said locking holes when said handle is attached to said frame body from a first direction, and to move into a locking position when said handle is moved in a second direction after said handle has been attached to said frame body from said first direction;
  said holding jaw being adapted to align with said holding slot when said locking studs are fitted into said locking holes by attaching said handle to said frame body in said first direction, and to fit into said holding slot when said handle is moved in said second direction;
  said latch of said tray body being adapted to snap-fit into said latching hole when said handle has been moved in second direction to said locking position whereby said handle is kept from being moved in a direction opposite to said second direction, and also kept from being moved in another direction opposite to said first direction.

2. A dental impression tray as recited in claim 1, wherein a recess is formed between said holding jaw and said handle for receiving a tab formed by a part of said bottom plate of said frame body when said holding jaw is fitted into said holding slot of said tray body.

3. A dental mold frame as recited in claim 2, wherein said handle stem is bent into a prescribed shape.

* * * * *